(12) United States Patent
Kushnir et al.

(10) Patent No.: US 9,140,695 B2
(45) Date of Patent: Sep. 22, 2015

(54) METHODS FOR ANALYSIS OF FREE AND AUTOANTIBODY-BOUND BIOMARKERS AND ASSOCIATED COMPOSITIONS, DEVICES, AND SYSTEMS

(71) Applicant: University of Utah Research Foundation, Salt Lake City, UT (US)

(72) Inventors: Mark M. Kushnir, Salt Lake City, UT (US); Alan L. Rockwood, Riverton, UT (US); A. Wayne Meikle, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 179 days.

(21) Appl. No.: 13/676,980

(22) Filed: Nov. 14, 2012

(65) Prior Publication Data

US 2013/0183770 A1 Jul. 18, 2013

Related U.S. Application Data

(60) Provisional application No. 61/632,125, filed on Jan. 18, 2012.

(51) Int. Cl.
*G01N 33/53* (2006.01)
*G01N 33/539* (2006.01)
*G01N 33/541* (2006.01)

(52) U.S. Cl.
CPC .......... *G01N 33/5306* (2013.01); *G01N 33/539* (2013.01); *G01N 33/541* (2013.01)

(58) Field of Classification Search
None
See application file for complete search history.

(56) References Cited

U.S. PATENT DOCUMENTS

| 7,632,686 | B2 | 12/2009 | Anderson |
| 7,807,172 | B2 | 10/2010 | Hoofnagle et al. |
| 2009/0042213 | A1* | 2/2009 | Hoofnagle et al. ............ 435/7.1 |
| 2009/0148951 | A1* | 6/2009 | Zhang et al. .................... 436/86 |
| 2009/0253156 | A1* | 10/2009 | Patton et al. .................... 435/15 |
| 2010/0028340 | A1* | 2/2010 | Mueller et al. ............. 424/133.1 |
| 2010/0120169 | A1* | 5/2010 | Dodds et al. .................. 436/500 |

OTHER PUBLICATIONS

Nicol et al., Use of an immunoaffinity-mass spectrometry-based approach for the quantification of protein biomarkers in serum samples of lung cancer patients, Molecular & Cellular Proteomics 7:1974-1982, 2008.*

Spencer et al., Serum Thyroglobulin Autoantibodies: Prevalence, influence of serum thyroglobulin measurement, and prognostic significance in patients with differentiated thyroid carcinoma, Journal of Clinical Endocrinology and Metabolism, 83(4):1121-1127, 1998.*

Venkiteshwaran et al., Selective precipitation assisted recovery of immunoglobulins from bovine serum using controlled-fouling crossflow membrane microfiltration, Biotechnology and Bioengineering, 101(5):957-966, 2008.*

* cited by examiner

*Primary Examiner* — Galina Yakovleva
*Assistant Examiner* — Andrea S Grossman
(74) *Attorney, Agent, or Firm* — Thorpe North & Western, LLP (57) ABSTRACT

The present invention provides methods, compositions, and kits associated with analyzing, enriching, and/or isolating a biomarker or analyte in a biological sample. In one aspect, for example, a method for determining a concentration of a biomarker in a biological sample can include binding any unbound biomarker with an antibody specific for the biomarker to form antibody-bound biomarker, enriching the antibody-bound biomarker and any endogenous autoantibody-bound biomarker to form an enriched fraction, identifying the biomarker in the enriched fraction, and determining the concentration of the biomarker in the biological sample. In one aspect, the concentration of the biomarker is derived from initially unbound biomarker and autoantibody-bound biomarker in the biological sample.

4 Claims, 5 Drawing Sheets

SEQUENCE LISTING

<160> NUMBER OF SEQ ID NOS: 5

<210> SEQ ID NO 1
<211> LENGTH: 12
<212> TYPE: PRT

```
<213> ORGANISM: Homo sapiens

<400> SEQUENCE: 1

Val Ile Phe Asp Ala Asn Ala Pro Val Ala Val Arg
1               5                   10

<210> SEQ ID NO 2
<211> LENGTH: 14
<212> TYPE: PRT
<213> ORGANISM: Homo sapiens

<400> SEQUENCE: 2

Phe Ser Pro Asp Asp Ser Ala Gly Ala Ser Ala Leu Leu Arg
1               5                   10

<210> SEQ ID NO 3
<211> LENGTH: 8
<212> TYPE: PRT
<213> ORGANISM: Homo sapiens

<400> SEQUENCE: 3

Leu Gly Asp Gln Glu Phe Ile Lys
1               5

<210> SEQ ID NO 4
<211> LENGTH: 11
<212> TYPE: PRT
<213> ORGANISM: Homo sapiens

<400> SEQUENCE: 4

Phe Pro Leu Gly Glu Ser Phe Leu Val Ala Lys
1               5                   10

<210> SEQ ID NO 5
<211> LENGTH: 24
<212> TYPE: PRT
<213> ORGANISM: Homo sapiens

<400> SEQUENCE: 5

Pro Val Pro Glu Ser Lys Val Ile Phe Asp Ala Asn Ala Pro Val Ala
1               5                   10                  15

Val Arg Ser Lys Val Pro Asp Ser
            20
```

METHODS FOR ANALYSIS OF FREE AND AUTOANTIBODY-BOUND BIOMARKERS AND ASSOCIATED COMPOSITIONS, DEVICES, AND SYSTEMS

PRIORITY DATA

This application claims the benefit of U.S. Provisional Patent Application Ser. No. 61/632,125, filed on Jan. 18, 2012, which is incorporated herein by reference in its entirety.

BACKGROUND OF THE INVENTION

The presence or absence of specific biomarkers can be predictive in the diagnosis and/or determination of a variety of conditions in an individual. As such, the accuracy of detection and quantification of a particular biomarker can be important for the correct diagnosis and treatment of an associated condition. In those cases where a biomarker is incorrectly identified in or its concentration is incorrectly determined in a biological sample, the individual can be improperly treated for a condition that is not present or can be left untreated for a condition that is present.

A variety of situations can make the detection of a biomarker problematic, both for the presence or absence of the biomarker, as well as the concentration level of the biomarker in the individual. One such situation can occur for individuals expressing autoantibodies to a biomarker in question. In such cases, the autoantibodies (AAb) can adversely affect the assay used to detect the biomarker. As one example, the measurement of thyroglobulin (Tg) is commonly used for the follow-up of patients treated for differentiated thyroid carcinoma (TC). Because thyroid tissue is the only source of Tg, total thyroidectomy and radioactive ablation should decrease serum concentrations of Tg to very low or undetectable levels. A rise of serum concentration of Tg in post-treatment patients is thus indicative of the recurrence of the TC. In a retrospective study on assessment of the utility of multiple potential biomarkers of the recurrence of TC, post-treatment Tg concentration was found to be the strongest independent predictor of the recurrence. One difficulty in using Tg as a biomarker is related to the presence of anti-Tg autoantibodies (Tg-AAb) in the blood of certain individuals. Tg antibodies were first described by Stokinger and Heidelberger in 1937, and subsequent research to date has not generated an effective commercial technique to overcome interference of Tg-AAb in testing for Tg. Current protocols to assess reliability of Tg measurements with immunoassays (IA) commonly test every specimen analyzed for Tg also for the presence of Tg-AAb.

Furthermore, it has been hypothesized that there might be a pathological and causative link between thyroid cancer coexistence and thyroid autoimmunity. Approximately 25% of patients with TC and up to 10% of individuals without TC are positive for Tg-AAb, and thus the presence of autoantibodies in samples tested for Tg by IA could cause false-negative results when epitopes used by the capture or detection antibody are occupied by the Tg-AAb. This can potentially cause misdiagnosis of the recurrence of TC.

SUMMARY

The present disclosure provides methods for analyzing, enriching, and/or isolating a biomarker or analyte in a biological sample, whether the sample contains autoantibody-bound biomarker, autoantibody-free biomarker (not bound to autoantibody), or both autoantibody-bound biomarker and autoantibody-free biomarker. The present scope additionally includes compositions, devices, kits, and systems relating to such analysis, enrichment, and/or isolation. In one aspect, for example, a method for determining a concentration of a biomarker in a biological sample is provided. Such a method can include binding any unbound biomarker with an antibody specific for the biomarker to form antibody-bound biomarker complexes, enriching the antibody-bound biomarker and any endogenous autoantibody-bound biomarker to form an enriched fraction, identifying the biomarker in the enriched fraction, and determining the concentration of the biomarker in the biological sample. In one aspect, the concentration of the biomarker is derived from initially unbound biomarker and autoantibody-bound biomarker in the biological sample.

Various techniques for enriching the biomarker are contemplated, and any such technique is considered to be within the present scope. In one aspect, identifying the biomarker in the enriched fraction can further include digesting the antibody-bound biomarker and the endogenous autoantibody-bound biomarker complexes and detecting a product of digestion to identify and quantify the biomarker. In one specific aspect, determining the concentration of the biomarker in the biological sample can include detecting the concentration of the product of digestion in the enriched fraction. In another aspect, enriching can further include enriching the antibody-bound biomarker and any endogenous autoantibody-bound biomarker to form an enriched fraction. In yet another aspect, enriching can include precipitating the antibody-bound biomarker and any endogenous autoantibody-bound biomarker. In yet another aspect, enriching can include separation of the biomarker from the biological sample using anti-biomarker antibody, protein A, protein G, protein L, anti-immunoglobulin antibody, or a combination thereof. In a further aspect, enriching can include precipitating the antibody-bound biomarker and any endogenous autoantibody-bound biomarker along with a chemical precipitation of immunoglobulins, or alternatively unrelated proteins can be separated from solution by a chemical precipitation, while the antibody-bound and autoantibody-bound biomarker is kept in solution.

Various biomarkers are contemplated, and any such biomarker for which autoantibodies can negatively affect a detection assay is considered to be within the present scope. Non-limiting examples of such biomarkers can include thyroglobulin, insulin, cardiac troponin I, tumor suppressor protein p53, tumor-associated antigens, anti-retinal autoantibodies, markers of age-related macular degeneration, and the like. In one specific aspect, the biomarker is thyroglobulin.

In another aspect, identifying the biomarker can be an immune based method such as, for example, RIA, ELISA, EMIT, chemiluminescence immunoassay, or the like, including combinations thereof. In yet another aspect, identifying the biomarker can be performed using mass spectrometry. One specific example of mass spectrometry that may be useful is tandem mass spectrometry; another example is high mass accuracy/high mass resolution mass spectrometry (e.g. Orbitrap™, Thermo Scientific).

The present disclosure additionally provides a method for determining a concentration of thyroglobulin in a biological sample. Such a method can include binding any unbound thyroglobulin with an antibody specific for thyroglobulin to form antibody-bound thyroglobulin, enriching the antibody-bound thyroglobulin and any endogenous autoantibody-bound thyroglobulin to form an enriched fraction, identifying the thyroglobulin in the enriched fraction, and determining the concentration of the thyroglobulin in the biological sample.

In one aspect, identifying the thyroglobulin in the enriched fraction can further include digesting the antibody-bound thyroglobulin and the endogenous autoantibody-bound thyroglobulin complexes, and detecting a product of digestion to identify thyroglobulin. Non-limiting examples of products of thyroglobulin digestion can include SEQ ID 001, SEQ ID 002, SEQ ID 003, SEQ ID 004, SEQ ID 005, or a combination thereof.

The present disclosure additionally provides a kit for determining a concentration of thyroglobulin in a biological sample. Such a kit can include a housing, an antibody preparation including at least one first antibody specific for thyroglobulin, magnetic beads having at least one second antibody coupled thereto, the antibody specific to at least one epitope of a thyroglobulin fragment, and instructions describing using the antibody preparation and the magnetic beads, the instructions also describing enrichment and digestion of thyroglobulin. In one specific aspect, the second antibody is specific for SEQ ID 001.

DETAILED DESCRIPTION

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

It must be noted that, as used in this specification and the appended claims, the singular forms "a," "an," and "the" include plural referents unless the context clearly dictates otherwise. Thus, for example, reference to "an antibody" includes one or more of such antibodies or synthetic binders, and reference to "the protein" includes reference to one or more of such proteins or small molecular biomarkers.

Definitions

In describing and claiming the present invention, the following terminology will be used in accordance with the definitions set forth below.

As used herein, the term "autoantibody" refers to an antibody produced by the immune system of a subject that is directed against one or more of the subject's own biomarkers.

As used herein, the term "synthetic binder" refers to an aptamer, synthetic binding site, cofactor, or combinations of the above.

As used herein, the term "free" and "unbound" when used in reference to a biomarker's association with an antibody can be used interchangeably, and relate to a biomarker in a biological sample or in a subject that is not complexed or otherwise bound to an autoantibody specific for the biomarker. Thus, in some aspects a "free biomarker" or an "unbound biomarker" can refer to a biomarker that is not bound by any antibody whatsoever. In other aspects, these terms can refer to a biomarker that is not bound by autoantibody, but may be bound by antibody introduced into a biological sample according to the present methods.

As used herein, the term "antibody" refers to an immunoglobulin specifically immunoreactive to a given antigen. The term "antibody" is intended to include whole antibodies of any isotype (IgG, IgA, IgM, IgE, IgY, etc.), and fragments thereof. It is noted that antibodies can be derived from a variety of animal species, and that antibodies from any species that can be beneficially utilized according to aspects of the present disclosure are considered to be within the present scope. In some non-limiting aspects, shark and/or camelid antibodies can be used. An "antibody" of the present invention also includes an antibody preparation. In addition to this traditional definition, in some aspects the term "antibody" can be used to encompass other molecules and structures that can serve a similar binding purpose. Non-limiting examples of non-traditional antibodies can include proteins, aptamers, synthetic binding sites, cofactors, and the like, including combinations thereof.

As used herein, the term "subject" refers to a mammal that may benefit from the techniques according to aspects of the present disclosure. Examples of subjects include humans, and may also include other animals such as horses, pigs, cattle, dogs, cats, rabbits, and aquatic mammals.

As used herein, the term "biological sample" refers to any sample of a biological nature obtained from a subject that may contain a biomarker. Non-limiting examples include biological fluids and biological tissues such as blood, blood serum, plasma, saliva, semen, vaginal fluid, lymph, urine, lachrymal fluid, cancerous tissue, non-cancerous tissue, tumor tissue, skin tissue, and the like.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Invention

The present disclosure provides methods for analyzing, enriching, and/or isolating a biomarker or analyte in a biological sample, whether the sample contains autoantibody-bound biomarker, autoantibody-free biomarker, or both autoantibody-bound biomarker and autoantibody-free biomarker. The present scope additionally includes compositions, devices, kits, and systems relating to such analysis, enrichment, and/or isolation.

In many traditional peptide purification schemes, the target peptide is usually used as bait to capture an antibody directed to a target analyte. The target peptide is generally separated from the antibody in subsequent processing; however in some cases the target peptide may not be entirely removed. This can interfere with subsequent analysis because the target peptide is an impurity that can be chemically the same as the target analyte. The purification schemes according to aspects of the present disclosure overcome this problem by using a modified bait. For example, if the bait is an isotopically labeled version of the target analyte, then it can be separated from the target analyte by mass spectrometry. Possible interference from the internal standard can also be avoided by using a labeled bait having a different mass from the internal standard. Similarly, if the bait is an extended sequence of the target analyte, then the bait should not interfere with a subsequent analysis by mass spec.

As has been described, the accuracy of an assay for the detection of a biomarker in a subject can be greatly reduced by the presence of autoantibodies directed to the biomarker. In some cases an assay can show and absence of the biomarker when it is in fact present in the biological sample, thus generating a false-negative result. The inventors have discovered that the addition of antibody specific for the biomarker to the biological sample prior to enrichment can actually increase the accuracy of biomarker detection is such assays. This counter-intuitive addition of antibody can increase biomarker enrichment to a degree that allows clinical-level diagnostic results with increased accuracy and degree of confidence.

In one aspect, for example, a method for determining a total amount of a biomarker in a biological sample is provided. It is intended that the scope of this method include the testing of biological samples having no biomarker, free biomarker (i.e. not bound by autoantibody), and/or autoantibody-bound biomarker. In other words, the present methods allow the clinically accurate assaying of a biological sample for those subjects having autoantibodies for the biomarker and for those subjects lacking autoantibodies for the biomarker. Thus, a negative result demonstrates the actual absence of the biomarker in the subject as opposed to a potential false-negative result whereby the biomarker is present but bound to autoantibodies.

Various method steps are contemplated to accomplish this enhanced biomarker detection assay. In one aspect, for example, the method can include binding any unbound biomarker with an antibody specific for the biomarker to form antibody-bound biomarker, and enriching the antibody-bound biomarker and any endogenous autoantibody-bound biomarker to form an enriched fraction. In some aspects, the total amount of the biomarker in the enriched fraction can include antibody-bound biomarker where the antibody includes only antibodies added to the biological sample in vitro. In other aspects, the total amount of the biomarker in the enriched fraction can include AAb-bound biomarker and antibody-bound biomarker (i.e. the added antibody). In yet other aspects, the total amount of the biomarker in the enriched fraction can include only AAb-bound biomarker. Additionally, in some aspects the biological sample can include no biomarker or an amount of biomarker that is below the detection threshold. It is thus contemplated that the present method includes the testing of biological samples that test negative for the presence of the biomarker.

Once the enriched fraction has been obtained, the biomarker can be detected in the fraction. In one aspect, detection can thus include verification of the presence of the biomarker in the enriched fraction. In another aspect, detection can also include a determination of the amount or concentration of biomarker in the enriched fraction. As such, the total concentration of biomarker can be determined from the proportion obtained in the enriched fraction.

Various biomarkers are contemplated for detection and/or analysis according to aspects of the present disclosure. It is noted that any biomarker for which autoantibodies may affect detection and/or measurement is considered to be within the present scope.

For example, the biomarker can include, without limitation, biopolymers, proteins, peptides, small molecules, and the like. Specific non-limiting examples of such biomarkers can include thyroglobulin, insulin, cardiac troponin I, tumor suppressor protein p53, tumor-associated antigens, anti-retinal autoantibodies, markers of age-related macular degeneration, and the like.

Thyroglobulin (Tg) is one example of a biomarker that can be beneficially assayed according to aspects of the present disclosure. It should be noted that the following description and discussion relating to Tg is exemplary, and that any biomarker that can be so assayed is considered to be within the present scope. As has been described, anti-Tg autoantibodies (Tg-AAb) in the blood of certain individuals can affect the accuracy of Tg biomarker testing using traditional assay methods. The current techniques overcome the interference of Tg-AAb and allow the quantification of Tg in a biological sample that is specific, sensitive, and robust enough for routine use in clinical laboratories.

As has been described, one difficulty for traditional assay techniques in the analysis of Tg in a biological sample is related to multiple forms of Tg that can be present in circulating blood, namely the free and Tg-AAb bound Tg. It has been shown that at least nineteen epitopes on the Tg molecule could participate in autoantibody binding. Considering the inter-individual differences in these epitopes, along with the affinity of Tg-AAbs towards Tg, and the task of measuring Tg (and other biomarkers for which AAb can be present in circulation) can be very complex, in some cases more complex than for many other endogenous biomarkers. Because the presence of Tg (free or AAb-bound) is indicative of the recurrence of thyroid cancer (TC), low concentrations of total Tg (free and AAb-bound) need to be accurately measured, and the existence in samples of multiple forms of Tg and Tg-AAb complicates the task for traditional methods. In many cases, concentrations of Tg above 1 ng/mL can be considered as indicative of the recurrence of thyroid cancer in such patients. In one aspect, Tg can be measured in concentrations at least as low as 0.5 ng/mL using techniques according to aspects of the present disclosure.

As has been described, free biomarker and any AAb-bound biomarker present in the biological sample can be enriched by binding any free or unbound biomarker with an antibody capable of forming a complex with the biomarker. Any form or type of antibody specific for the biomarker can be utilized. In one aspect, for example, the antibody can be polyclonal, monoclonal, or a mixture thereof. Additionally, the antibody can be derived from any appropriate species, including, without limitation, rabbit, goat, chicken, mouse, fish, cartilaginous fish, camelid, human, and the like, including combinations thereof.

Biomarker enrichment can be performed by any technique that facilitates the pooling of biomarker that is not AAb-bound and any AAb-bound biomarker present into a total biomarker concentration or amount. By concentrating the Abb-bound biomarker and the free biomarker into a single fraction, total concentration of the biomarker in a sample can be determined. Additionally, in some cases all biomarkers in the biological sample can be bound by biomarker-AAb, and little to no free biomarker is present in circulation.

Various techniques for enrichment of a biomarker can be utilized, and any such technique that facilitates the pooling of free biomarker with AAb-bound biomarker is considered to be within the present scope. In one aspect, for example, pooling of the free and AAb-bound complexes can be accomplished by binding the free biomarker with antibody and enriching by maintaining the pooled complexes in solution while unrelated constituents from the biological sample are separated from solution. As one specific example, unrelated proteins can be separated from sample by a chemical precipitation, while maintaining the biomarker-antibody and biomarker-AAb complexes in solution. One non-limiting example of such a chemical precipitation can include caprylic acid, however any reagent capable of precipitating albumin and other abundant proteins while allowing Tg and IG to remain in solution is considered to be within the present scope.

In another aspect, the pooled complexes can be enriched and separated from solution by precipitation. Various techniques are contemplated to facilitate precipitation or separation of the pooled complexes. Non-limiting examples can include precipitation techniques utilizing anti-biomarker antibody, protein A, protein G, protein L, anti-immunoglobulin antibodies, or a combination thereof. In one specific aspect, enrichment can be accomplished by coprecipitating Tg with a precipitation of IG, such as, for example, an ammonium sulfate precipitation. As such, Tg-complexes can be produced as has been described using any antibody capable of forming a complex with Tg. Such Tg-antibody complexes can be coprecipitated along with IG.

Returning to Tg, enrichment can be based on the discovered phenomenon that substantially all forms of Tg present in a biological sample can be concentrated in a single fraction, while at the same time a large fraction of non-targeted blood proteins can be depleted from the samples. Various strategies that can be used to enrich Tg are described above. As one specific example, enrichment from a biological sample can be accomplished using Affinity-Assisted Precipitation (AAP). As has been described, anti-Tg antibodies are added to the biological sample to Ab-bind any unbound Tg biomarker. Following binding of any unbound or free Tg with Tg-Ab, both AAb-bound Tg and Ab-bound Tg (i.e. the pooled complexes) can be co-precipitated with ammonium sulfate along with IG. As such, the addition of anti-Tg antibody of any species to the sample can enhance Tg precipitation, thus increasing the accuracy of the detection assay. The supernatant following precipitation can be discarded and the Tg-containing precipitates can be further processed. Effects of concentration of the antibody and amount of ammonium sulfate on distribution of Tg, total protein, albumin, and IgG between the supernatants and the precipitates are shown in FIGS. 1 and 2.

Figure 1A:
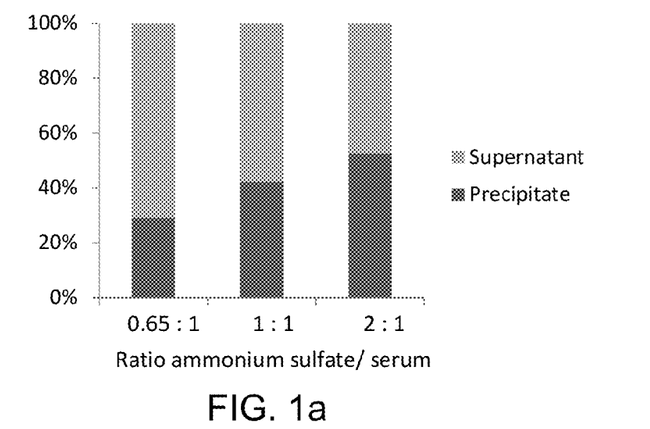
FIG. 1a provides results showing the total protein content between precipitates and supernatants according to one aspect of the present disclosure.
Figure 1B:
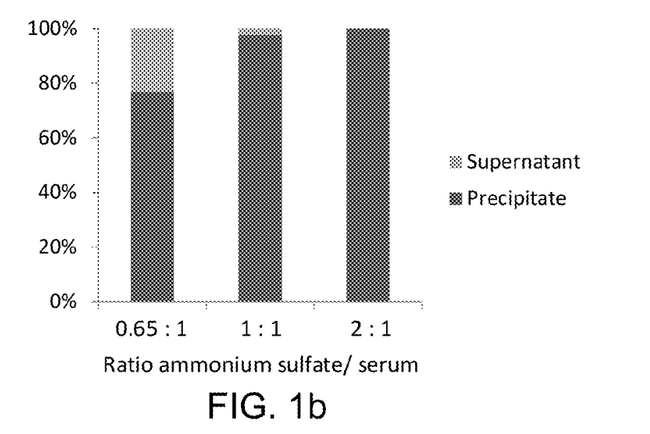
FIG. 1b provides results showing the total protein content and distribution of IG between precipitates and supernatants according to one aspect of the present disclosure.
Figure 1C:
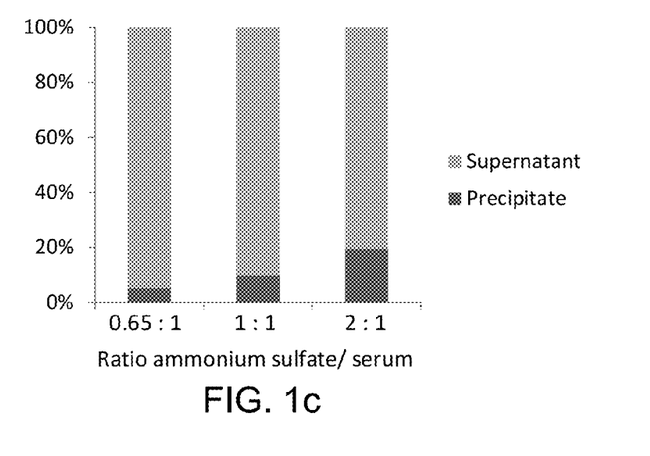
FIG. 1c provides results showing the total protein content and distribution of albumin between precipitates and supernatants according to one aspect of the present disclosure.

FIG. 1a-c show the total protein content and distribution of Tg and IG between precipitates and supernatants evaluated in samples containing and not containing Tg-AAb using different ammonium sulfate/serum ratios, with and without anti-Tg antibodies. Percent distribution of total proteins (FIG. 1a), IgG (FIG. 1b), and albumin (FIG. 1c) between the supernatants and the precipitates are shown.

Figure 2A:
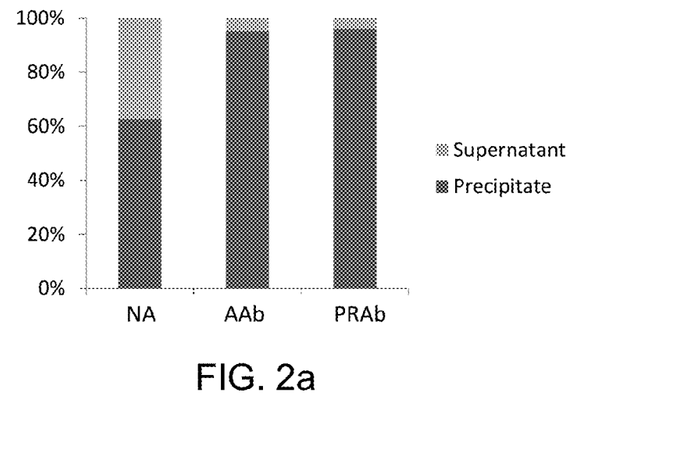
FIG. 2a provides results showing the percent distribution of thyroglobulin between the supernatants and the precipitates in biological sample for no antibody (NA), Tg-autoantibody (AAb), and polyclonal rabbit antibody (PRAb) added to the sample with ratio of ammonium sulfate/serum 0.65:1 according to one aspect of the present disclosure.
Figure 2B:
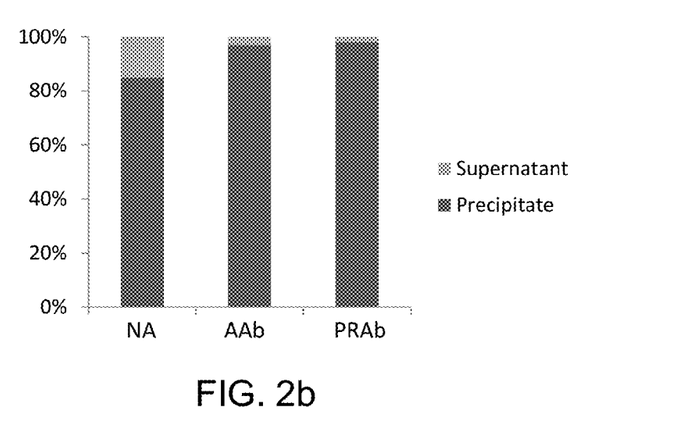
FIG. 2b provides results showing the percent distribution of thyroglobulin between the supernatants and the precipitates in biological sample for no antibody (NA), Tg-autoantibody (AAb), and polyclonal rabbit antibody (PRAb) added to the sample with ratio of ammonium sulfate/serum 1:1 according to one aspect of the present disclosure.
Figure 2C:
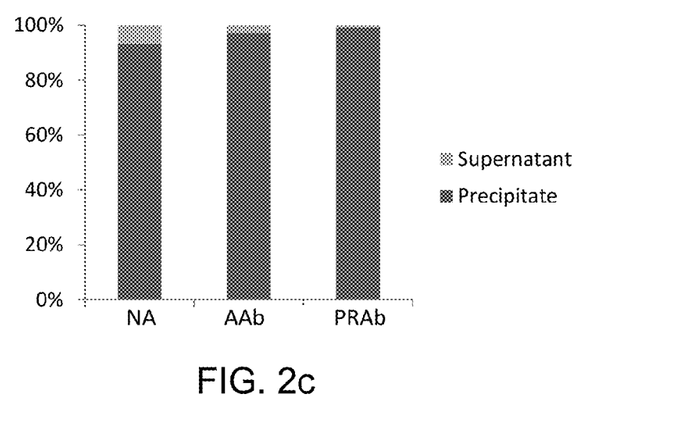
FIG. 2c provides results showing the percent distribution of thyroglobulin between the supernatants and the precipitates in biological samples for no antibody (NA), Tg-autoantibody (AAb), and polyclonal rabbit antibody (PRAb) added to the sample with ratio of ammonium sulfate/serum 2:1 according to one aspect of the present disclosure.

FIG. 2a-c show thyroglobulin concentration measured by LC-MS/MS method. The percent distribution of thyroglobulin between the supernatants and the precipitates in the biological samples are shown for no antibody (NA), Tg-autoantibody (AAb), and polyclonal rabbit antibody (PRAb) added to the sample. In FIG. 2a the ratio of ammonium sulfate to serum is 0.65:1; in FIG. 2b the ratio of ammonium sulfate to serum is 1:1; and in FIG. 2c the ratio of ammonium sulfate to serum is 2:1.

It is thus observed that in serum and plasma samples containing Tg-AAb, Tg bound to AAb is separated into the IG-containing fraction. Higher ratios of ammonium sulfate to serum/plasma increase efficiency of Tg precipitation, also resulting in enhanced precipitation of other proteins. A large fraction of Tg in samples of patients not having Tg-AAb also precipitated (FIG. 1); this may be through co-precipitation with IG, such as precipitation of a Tg/antibody complex formed by non-specific binding of antibody to Tg. In samples not containing IG, Tg did not precipitate and remained in solution.

Adding anti-Tg antibodies to biological samples can thus increase the efficiency of the enrichment. Without intending to be bound to any scientific theory, this may be due to the binding of free Tg to the exogenous antibody and partitioning of the antibody-Tg complexes into the IG fraction. As an example, Tg enrichment based on precipitation of Tg with IG using ammonium sulfate can increase Tg enrichment to clinical levels, while at the same time reducing the total concentration of proteins by up to 70%. The ratio of ammonium sulfate to serum/plasma during Tg precipitation can be adjusted to assure completeness of precipitation of Tg, while minimizing precipitation of albumin and other serum/plasma proteins as is shown in FIGS. 1a-c and 2a-c. Additionally, it is noted that enrichment via the addition of antibody was particularly enhanced in samples containing higher concentrations of Tg, such as, for example, above 50 ng/ml.

The ammonium sulfate precipitation produces a powdery precipitate that, after centrifugation, results in a dense protein pellet. Once the supernatant is removed, the precipitate is easily re-dissolved in water. As such, this precipitation enrichment concentrates all forms of Tg present in serum (free and AAb-bound) into a single fraction, reduces sample complexity (albumin and large fraction of serum/plasma proteins are removed with the supernatant), and allows sample matrix exchange prior to subsequent sample processing.

Following enrichment, the sample can be processed to varying degrees. In one aspect, for example, the biomarker can be directly assayed from the enriched fraction. In another aspect, the enriched fraction can be further processed to facilitate biomarker detection and/or quantification. In one specific example relating to Tg, re-dissolved enriched biomarker can be denatured, reduced, and digested with, for example, sodium deoxycholate (DOC), dithiothreitol (DTT), Trypsin, endoproteinase Lys-C, endoproteinase Asp-N, thrombin, and the like, including combinations thereof.

In some cases, the concentration of DOC can affect the extent of denaturing and the recovery of the targeted peptide. Lack of DOC can lead to incomplete digestion, while excess DOC can increase sample viscosity, thus affecting the immunoaffinity enrichment of the biomarker. The denaturing, reduction, and digestion can be optimized to facilitate rapid, complete, and reproducible digestion of Tg.

Following digestion, the sample can be processed to varying degrees. In one aspect, for example, the biomarker can be directly assayed from the digested fraction. In another aspect, the enriched fraction can be further processed to facilitate biomarker detection and/or quantification. For example, protein can be further separated to improve the processing and detection of the biomarker or digested portions of the biomarker. In one aspect, for example, chromatographic separation can be utilized to further enrich the biomarker or biomarker fragments. Various chromatography techniques are known, and any such technique is considered to be within the present scope. In one specific aspect, one-dimensional reversed phase chromatography can be used. While such techniques can be useful depending on the biomarker and specifics of the given separation procedure, in other aspects multidimensional separations can be used to improve signal-to-noise ratio and reduce background noise. In one aspect, two-dimensional separation can be optimized for the targeted biomarker using two chromatographic columns using complementary retention mechanisms with second dimension separation under ultra-high performance liquid chromatography (UPLC) conditions. In one specific aspect, good selectivity can be achieved by combining a one-dimensional column with weak retention to a two-dimensional column strongly retaining the peptide. The separation conditions can be further optimized to provide a good separation from other endogenous peaks, while maintaining a short analysis time. Additionally, in some aspects other types of separation, in addition to the one-dimensional separation described above, can be utilized as well. Non-limiting examples of such separation techniques include electrophoresis, capillary electrophoresis, nano-HPLC separation, slab gel electrophoresis, ion mobility, or any combination of the techniques in either an online or offline format.

The complexity of the biological sample, the enriched fraction, the digested fraction, or any sample following subsequent separation can also be further reduced by a variety of techniques. Non-limiting examples can include immunoaffinity depletion (for the removal of abundant proteins) and immunoaffinity capture (to isolate or enrich the biomarker or biomarker fragments), which can be used to reduce complexity of biological samples. Other techniques can utilize online and offline immunoaffinity enrichment with antibody immobilized on polymeric and/or magnetic beads. Such techniques can be utilized to separate the targeted products from the sample, or they can be used to separate non-targeted products from the sample. Compared to online approaches, off-line immunoaffinity enrichment can provide increased flexibility in terms of selection of carriers, antibodies, assay formats, and experimental conditions.

In one specific aspect, Tg or a Tg product can be enriched from the tryptic digests using anti-peptide antibody conjugated to magnetic beads. Following elution from the beads, the products can be analyzed to determine the presence and concentration in the sample. In one aspect, the analysis can be by a 2D-LC-MS/MS method.

As has been described, biomarker detection can be accomplished using all of the biomarker, substantially all of the biomarker, or a fragment of the biomarker. The present scope is not, therefore, limited to specific biomarkers or portions of biomarkers. In the case of Tg, the sequences described herein are merely exemplary, and any fragment detectable with some form of antibody is considered to be within the present scope. As one example, immunoaffinity enrichment with polyclonal anti-peptide antibody showed binding for the capture of VIFDANAPVAVR peptide (SEQ ID 001) from serum digests with high recovery. Non-limiting examples of other peptide fragments from Tg can include FSPDDSAGASALLR (SEQ ID 002), LGDQEFIK (SEQ ID 003), FPLGESFLVAK (SEQ ID 004), and the like.

Enrichment conditions can be optimized by varying the amount of antibody, magnetic beads, serum volume, composition and conditions of the capture, the washes and the elution. Additionally, interference from nonspecifically bound peptides can be resolved by optimizing the wash and the elution conditions. The immunoaffinity enrichment allows selective capture and elution of the peptide resulting in substantial enhancement of the sensitivity and specificity of the method.

Accordingly, in one specific aspect an assay format can include (i) addition to biological samples of anti-Tg antibody; (ii) enrichment of Tg through an enrichment technique such as precipitation; (iii) re-dissolving the precipitate with a solvent containing internal standard; (iv) denaturing, reducing, and digesting; (v) enrichment of the biomarker or biomarker fragments using anti-peptide antibody conjugated to magnetic beads; and (vi) removal of non-specifically bound peptides by washing the beads. In some aspects the method can also include (vii) elution of the targeted biomarker or biomarker fragment, followed by (viii) biomarker analysis, such as by 2DLC-MS/MS.

Regarding HPLC separation, it is noted that a variety of techniques can be utilized and all such techniques are considered to be within the present scope. In one aspect, for example, a first separation can be performed on an HPLC column that weakly retains a target analyte, and a second separation can be performed on a column that strongly retains the target analyte.

It is noted that any technique for detecting a biomarker or biomarker fragment capable of use with aspects of the present disclosure are considered to be within the present scope. In one aspect, for example, the detection can include an immune-based method such as, for example, RIA, ELISA, EMIT, chemiluminescence immunoassay, and the like, including combinations thereof. In another aspect, mass spectrometry can be used. Tandem mass spectrometry, for example, can be used for quantitative analysis of peptides in biological samples due to high sensitivity and specificity. High mass accuracy/high mass resolution mass spectrometers (e.g. Orbitrap™, Thermo Scientific) also can be utilized for analysis. Generally, a product of digestion can be purified using separation techniques and ionized to generate ions detectable by mass spectrometry, where the concentration of peptides is determined by mass spectrometry, and amount detected is related to the amount of biomarker in the test sample. The ions can be single charged or multiple charged. In one aspect, ions selected in the first stage of mass analysis can be monoisotopic or isotopic. In another aspect, ions selected in the second stage of mass analysis can be monoisotopic or isotopic. Additionally, it is contemplated that in some cases ions selected in all following stages of mass analysis can be monoisotopic or isotopic.

Figure 3:
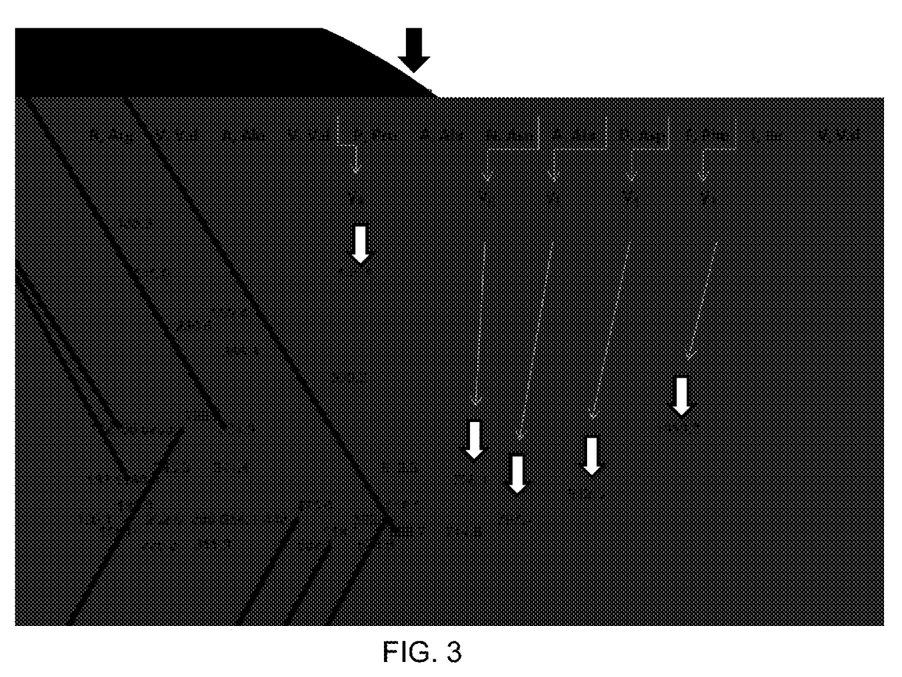
FIG. 3 provides a product ion mass spectrum of thyroglobulin-specific peptide VIFDANAPVAVR (SEQ ID 001) according to one aspect of the present disclosure.
Figure 4:
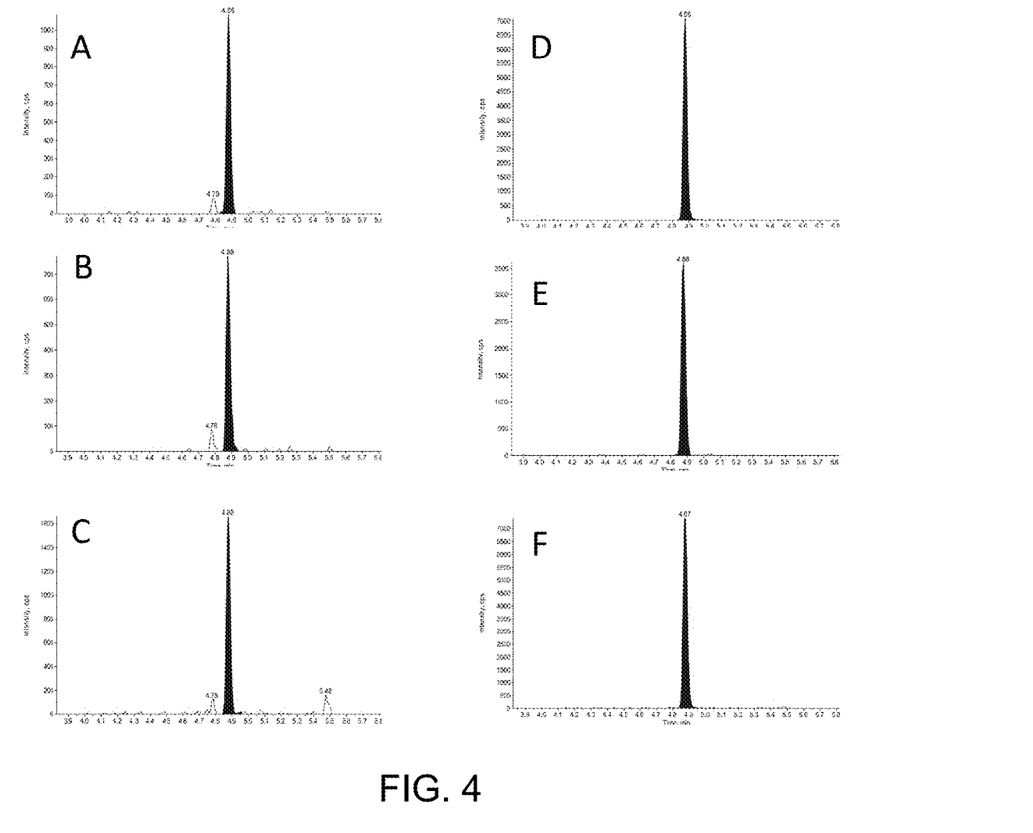
FIG. 4 shows chromatograms of biological samples containing 5 ng/mL of thyroglobulin according to one aspect of the present disclosure.

As an example, product ion mass spectrum of the Tg-specific peptide VIFDANAPVAVR (SEQ ID 001) is shown in FIG. 3. The solid arrow points to a double-charged parent ion, and the outlined arrows point to the major product ions. Additionally, multiple reaction monitoring chromatograms of the mass transitions of VIFDANAPVAVR (SEQ ID 001) are shown in FIG. 4 in biological samples containing 5 ng/mL of thyroglobulin. Mass transitions of the VIFDANAPVAVR (SEQ ID 001) peptide are m/z 636.36/1059.56 (A), 636.36/912.49 (B), 636.36/541.35 (C); and the internal standard m/z 639.34/1065.56 (D), 639.84/1066.56 (E), 639.34/918.48, 639.34/547.34 (F).

In one aspect, a detected ion can have an m/z ratio of 636.3595+/−0.5, 636.8634+/−0.5, 637.3673+/−0.5, 637.8712+/−0.5, or a combination thereof. In another aspect, one or more detected ions can be monoisotopic or isotopic ions such as, for example, ions with m/z of 541.3457+/−0.5, 542.3535+/−0.5, 543.3613+/−0.5, 544.3691+/−0.5; 612.3828+/−0.5, 613.3906+/−0.5, 614.3984+/−0.5, 615.406275+/−0.5; 726.4257+/−0.5, 727.4335+/−0.5, 728.4413+/−0.5, 729.4491+/−0.5; 797.4628+/−0.5, 798.4706+/−0.5, 799.4784+/−0.5, 800.4862+/−0.5; 912.4898+/−0.5, 913.4976+/−0.5, 914.5054+/−0.5, 915.5132+/−0.5; 1059.5582+/−0.5, 1060.5660+/−0.5, 1061.5738+/−0.5, 1062.5816+/−0.5; 1172.6422+/−0.5, 1173.6500+/−0.5, 1174.6578+/−0.5, 1175.6656+/−0.5, or a combination thereof.

Data of experiments of the evaluation of the assay imprecision are summarized in Table 1. The total assay imprecision at the evaluated concentrations was less than 10%; imprecision of Tg measurements in QC samples analyzed over 16 days was <14%. The LOQ and LOD of the method were 0.5 and 0.25 ng/mL (0.76 and 0.38 fmol/mL of the Tg dimer), respectively. The method was linear up to 1045 pg/mL with inaccuracy at the highest level <10%. No carryover was observed following an injection of a blank sample after a standard containing 1045 ng/mL (1.58 pmol/mL) of Tg.

TABLE 1

Within-run, between-run and total imprecision of LC-MS/MS method for thyroglobulin.

| Sample | Concentration, ng/mL | Within-run, % | Between-run/day, % | Total, % |
|---|---|---|---|---|
| Low 1# | 2.1 | 6.75 | 3.67 | 7.69 |
| Low QC 1* | 2.3 | na | 13.9 | na |
| Low 2# | 5.7 | 6.87 | 5.96 | 9.10 |
| Medium QC 2* | 6.5 | na | 10.5 | na |
| Medium# | 14.8 | 6.56 | 5.40 | 8.50 |
| High# | 399 | 3.56 | 1.71 | 3.95 |
| High QC* | 172.8 | na | 3.5 | na |

Samples analyzed in three replicates per day over five days
*Samples analyzed in one replicate per day, over 20 days As such, a biomarker fragment can be used as a surrogate marker for the quantification of the biomarker itself. In the case of Tg, for example, VIFDANAPVAVR (SEQ ID 001) can used as a surrogate marker for quantification of Tg (FIG. 4). Advantages of the VIFDANAPVAVR (SEQ ID 001) peptide for quantitation are in the ability to achieve a quantitative yield of the peptide with tryptic digestion, and in the absence in its sequence of amino acids that could be post-translationally modified.

In another aspect, thyroglobulin from the biological sample can be digested to form peptide FSPDDSAGASALLR (SEQ ID 002). In this case, a detected ion can be monoisotopic or isotopic and have an m/z ratio of 703.8497+/−0.5, 704.3536+/−0.5, 704.8575+/−0.5, 705.3614+/−0.5, or a combination thereof. Additionally, one or more detected ions can be monoisotopic or isotopic, non-limiting examples of which have m/z of 1406.6910+/−0.5, 1407.6988+/−0.5, 1408.7067+/−0.5, 1409.7145+/−0.5, 1259.6226+/−0.5, 1260.6304+/−0.5, 1261.6383+/−0.5, 1262.6461+/−0.5, 1172.5906+/−0.5, 1173.5984+/−0.5, 1174.6063+/−0.5, 1175.6141+/−0.5, 1075.5378+/−0.5, 1076.5456+/−0.5, 1077.5535+/−0.5, 1078.5613+/−0.5, 960.5109+/−0.5, 961.5187+/−0.5, 962.5266+/−0.5, 963.5344+/−0.5, 845.4839+/−0.5, 846.4917+/−0.5, 847.4996+/−0.5, 848.5074+/−0.5, 758.4519+/−0.5, 759.4597+/−0.5, 760.4676+/−0.5, 761.4754+/−0.5, 687.4148+/−0.5, 688.4226+/−0.5, 689.4305+/−0.5, 690.4383+/−0.5, 630.3933+/−0.5, 631.4011+/−0.5, 632.4090+/−0.5, 633.4168+/−0.5, 559.3562+/−0.5, 560.3640+/−0.5, 561.3719+/−0.5, 562.3797+/−0.5, 472.3242+/−0.5, 473.3320+/−0.5, 474.3399+/−0.5, 475.3477+/−0.5, 288.203+/−0.5, 289.2108+/−0.5, 290.2187+/−0.5, 291.2265+/−0.5, or a combination thereof.

In yet another aspect, thyroglobulin from the biological sample can be digested to form peptide LGDQEFIK (SEQ ID 003). In this case, a detected ion can have monoisotopic or isotopic and an m/z ratio of 475.2537+/−0.5, 475.7576+/−0.5, 476.2615+/−0.5, 476.7654+/−0.5, or a combination thereof. Additionally, one or more detected ions can be monoisotopic or isotopic, non-limiting examples of which have m/z of 949.4989+/−0.5, 950.5067+/−0.5, 951.5146+/−0.5, 952.5224+/−0.5, 836.4149+/−0.5, 837.4227+/−0.5, 838.4306+/−0.5, 839.4384+/−0.5, 779.3934+/−0.5, 780.4012+/−0.5, 781.4091+/−0.5, 782.4169+/−0.5, 664.3665+/−0.5, 665.3743+/−0.5, 666.3822+/−0.5, 667.3900+/−0.5, 536.3079+/−0.5, 537.3157+/−0.5, 538.3236+/−0.5, 539.3314+/−0.5, 407.2653+/−0.5, 408.2731+/−0.5, 409.2810+/−0.5, 410.2888+/−0.5, or a combination thereof.

In a further aspect, thyroglobulin from the biological sample can be digested to form peptide FPLGESFLVAK (SEQ ID 004). In this case, a detected ion can have monoisotopic or isotopic with an m/z ratio of 604.3403+/−0.5, 604.8442+/−0.5, 605.3481+/−0.5, 605.8520+/−0.5, or a combination thereof. Additionally, one or more detected ions can be monoisotopic or isotopic ions, non-limiting examples of which have m/z of 1207.6721+/−0.5, 1208.68+/−0.5, 1209.69+/−0.5, 1210.70+/−0.5, 1060.6037+/−0.5, 1061.61+/−0.5, 1062.62+/−0.5, 1063.63+/−0.5, 963.5510+/−0.5, 964.56+/−0.5, 965.57+/−0.5, 966.57+/−0.5, 850.4669+/−0.5, 851.47+/−0.5, 852.48+/−0.5, 853.49+/−0.5, 793.4454+/−0.5, 794.45+/−0.5, 795.46+/−0.5, 796.47+/−0.5, 664.4028+/−0.5, 665.41+/−0.5, 666.42+/−0.5, 667.43+/−0.5, 577.3708+/−0.5, 578.38+/−0.5, 579.39+/−0.5, 580.39+/−0.5, 430.3024+/−0.5, 431.31+/−0.5, 432.32+/−0.5, 433.33+/−0.5, or a combination thereof.

A stable-isotope-labeled analog of the targeted peptide was synthesized containing $5C_{13}/N_{15}$-labeled valine (V*), PVPESKVIFDANAPV*AVRSKVPDS (SEQ ID 005), and six amino acids of the sequence of Tg at the amino- and carboxy-terminuses of the tryptic digestion sites. The use of a structurally matched internal standard containing amino acids beyond the tryptic digestion sites allow improvement in assay precision by partially compensating for variation during the sample preparation and detection. Of particular note is that, like the target protein, the internal standard undergoes tryptic digestion.

The doubly charged precursor ions were used for the targeted peptide and the internal standard. Product ion mass spectrum of the VIFDANAPVAVR (SEQ ID 001) peptide is shown in FIG. 3. Multiple mass transitions of the targeted peptide, and the labeled internal standard, were utilized in to facilitate high specificity of the analysis. In subject samples with Tg concentrations above 10 ng/mL, product ions y3, y4, y5, y6, y8 provided adequate specificity, while the only mass transitions proved to be free of interferences in samples with concentration of Tg below 10 ng/mL were y3, y4, y8 (FIG. 3) and transitions corresponding to the first isotopes of the parent (m/z $M^{-2}$+O.5) and the product ions y3, y4, y8 (m/z M+1). Mass transitions of the stable isotope labeled internal standard corresponding to the above mass transitions of the unlabeled peptide also appear to be free of interference. Specificity of the analysis was evaluated by assessment of the ratios of the mass transitions of the targeted peptide and the internal standard. Other non-limiting examples of potential mass transitions that could be used in the analysis are monisotopic product ions, of non-monoisotopic parent ions or non-monoisotopic product ions of non-monoisotopic parent ions.

Other mass spectrometric techniques could also be used in the analysis, including but not limited to APCI and MALDI for ionization, and the use of either MS or MS/MS using various types of mass analyzers (e.g. quadrupole, time of flight, ion trap, QTOF, Orbitrap™ mass spectrometry, etc.) or combination of thereof.

Anti-Peptide Antibody Purification

In a further aspect, the present disclosure provides a method for purifying an antibody. Such a method can include a) providing a solution comprising an antibody, biological fluid, and a buffer substance; b) bringing the solution and an adsorbent (chemisorbent) with conjugated modified peptide (antigen) molecule in contact under conditions whereby the antibody binds to the conjugated modified peptide attached to adsorbent; and c) recovering the antibody from the adsorbent material by using a solution comprising a buffer substance and a salt.

In some aspects, the antibody can be captured with a modified peptide as opposed to the peptide to which the antibody was raised. Examples of modifications to such peptides can include, without limitation, extended sequences or functional groups at the amino or carboxyl or both amino and carboxyl terminuses. In another aspect, a modified peptide can be a peptide with one or more amino acids having functional group substitutions with desirable properties such as hydrophobisity, 3D structure, etc., thus allowing antibody-antigen binding. In yet another aspect, the modified peptide can be a peptide with one or more amino acids substituted with stable isotope labeled amino acids. In a further aspect, the modified peptide can be a peptide having extended amino acid sequences or functional groups at the amino or carboxyl, or both amino and carboxyl terminuses, and with one or more amino acids substituted with stable isotope labeled amino acid or unlabeled amino acid with desirable properties (e.g. hydrophobisity, 3D structure, etc.) allowing antibody-antigen binding. In yet a further aspect, a modified peptide can have extended amino acid sequences at the amino or carboxyl, or both amino and carboxyl terminuses with one or more amino acids substituted with other amino acids with desirable properties (e.g. hydrophobicity, 3D structure, etc.) allowing antibody-antigen binding. In yet another aspect, a modified peptide can include extended amino acid sequences at the amino or carboxyl, or both amino and carboxyl terminuses, which includes one or more amino acids substituted with stable isotope labeled amino acids.

EXAMPLES

Example 1

Preparation of Reagents, Standards, and Quality Control Samples

Standard of human Tg is purchased from AbD Serotec (Oxford, UK); stock solution of Tg is prepared at 1 mg/mL in 0.1% BSA, aliquoted in micro centrifuge tubes and stored at −70° C. Calibration standards of Tg are purchased from Beckman Coulter (Fullerton, Calif.); Tg concentrations in the standards are 0, 0.6, 6, 60, 150 ng/mL (0, 0.91, 9.1, 91 and 227 pmol/L). Rabbit polyclonal anti-Tg antibody is purchased from Covance (Princeton, N.J.) and diluted to 60 ng/µL with 0.1% BSA. Serum quality control samples are pooled human serum samples and contain 2, 6.5, and 170 ng/mL (3, 9.8, 258 pmol/L) of Tg. Working internal standard (IS) of "winged" peptide, sequence PVPESKVIFDANAPV*AVRSKVPDS (V* [13C5; 15N] (SEQ ID 005); mass shift 6 Da, RS synthesis Louisville, Ky.) is prepared at a concentration of 10 pg/µL (3.95 fmol/µL) in 20% acetonitrile in water.

Trypsin, formic acid (FA), dithiothreitol (DTT) and sodium deoxycholate (DOC) are purchased from Sigma-Aldrich (St. Louis, Mo.). All other reagents are of highest purity commercially available. Solvents are of HPLC grade, purchased from JT Baker (Phillipsburg, N.J.).

Example 2

Conjugation of Antibody to Magnetic Beads

Custom polyclonal rabbit anti-peptide antibody (Covance, Princeton, N.J.) is conjugated to Tosyl activated magnetic beads (DynaBeads M280, Life Technologies, Carlsbad, Calif.) according to the manufacturer's recommendations. Briefly, the beads are washed with PBS (pH 7.4) and re-suspended in a 1M ammonium sulfate solution containing 20

μg of antibody per milligram of beads. Beads are incubated at 37° C. for 20 hours, washed and incubated for 1 hour with blocking buffer containing 0.5% BSA for one hour and reconstituted to a concentration of 20 μg/μL. Antibody content on the beads is approximately 0.2 μg/μL.

Example 3

Trypsin Digestion Followed by Immunoaffinity Capture

Sample preparation is performed on a liquid handler (ep-Motion, Eppendorf, Hamburg, Germany). 5 μL (60 ng/μL) of rabbit anti-Tg antibody is added to a 500 μL aliquot of serum or plasma sample and the samples are incubated for one hour with mixing at 20° C. After the incubation, 350 μL of saturated ammonium sulfate solution is added to the samples, and Tg is precipitated along with immunoglobulins (IG). The samples are vortex-mixed for 10 min, centrifuged for 5 min at 15000 g, and the supernatants are discarded. The precipitates are reconstituted with 300 μL of water, 10 μL of internal standard (IS), 10 μL of 20 mM dithiothreitol, and 30 μL of 5% sodium deoxycholate are added, after which the samples are incubated at 60° C. for 30 min. After the incubation, 400 μL of 25 mM ammonium bicarbonate and 10 μL of trypsin (4 μg/μL) are added to the samples, and the samples are incubated for 4 hours at 37° C.

Magnetic beads are processed using a Magnetic Stand-96 (Life Technologies, Carlsbad, Calif.). After the digestion, 5 μL of the magnetic beads suspension is added to the samples, and the tubes are incubated with agitation at 20° C. for 8 h to allow antibody capture of the targeted peptide from the digest. The beads are washed with PBS (pH 7.4) three times, and the targeted peptide and the digested IS are eluted with 75 μL of 25 mM glycine (pH 2). The elutions are transferred into a 96-well plate, and 40 μL aliquots are injected on 2D LC-MS/MS. The overall time required for the sample preparation in a 96-well plate format is approximately 20 hours.

Example 4

2D HPLC Separation

2D HPLC separation is performed on an HPLC system including series 1260 and 1290 pumps (Agilent Technologies, Santa Clara, Calif.). A Zorbax XDB-CN 50×2.1, 5 μm HPLC column is used for the $1^{st}$ dimension separation with gradient of mobile phases A 98% to 87% A in 1.3 min (A, 10 mM formic acid in water; B, 10 mM formic acid in acetonitrile); the $2^{nd}$ dimension separation is performed on a Poroshell 120 EC-C18, 100×3, 2.7 μm column (both columns from Agilent Technologies) using a gradient of the same mobile phases 87 to 75% A in 2 min. The chromatographic separation is performed at 30° C.

Example 5

Mass Spectrometry Detection

Quantitative analysis is performed on an API 5500 triple-quadrupole mass spectrometer with a V-spray ionization source operated in a positive ion, multiple reaction monitoring (MRM) mode. Mass transitions monitored in the method are m/z 636.36/1059.56, 636.86/1060.56, 636.36/912.49, 636.86/913.49 and 636.36/541.35 for the VIFDANAPVAVR (SEQ ID 001) peptide, and m/z 639.34/1065.56, 639.84/1066.56, 639.34/918.48, 639.84/919.48, and 639.34/547.34, for the IS. The instrument settings are adjusted to maximize the sensitivity and the specificity of detection. The heating gas temperature is 450° C. The settings for the nebulizing gas (air), collision gas (nitrogen), and curtain gas (nitrogen) are 40, 9, and 40. The optimized declustering potential, collision energy, collision cell exit potential, and entrance potential are 100, 30, 30, and 10V. The dwell time for the mass transitions is 35 ms. The Q1 quadrupole is set to high resolution and Q3 quadrupole is set to unit resolution; 0.5 and 0.7 Da at half height, respectively. The total analysis time per sample is 6.5 min; the data acquisition time is started at 240 seconds, and the data are acquired for 90 seconds. The data are processed using Analyst software.

Total protein concentration is measured by spectrophotometric method using NanoDrop 8000 (Thermo Scientific, Wilmington, Del.). The concentrations of IgG and albumin are measured with a commercial IA, BN II (Dade Behring, Newark, Del.) and Modular Analytics (Roche Diagnostics, Indianapolis, Ind.), respectively. The Tg-AAb test is performed on instrument IMMULITE 2000 (Siemens, Tarrytown, N.Y.).

Example 6

Method Validation

Method validation consists of the evaluation of the imprecision, sensitivity, linearity, accuracy, recovery, carryover, ion suppression, and establishing reference intervals for Tg. Serum pools used during the method validation are prepared from remaining aliquots of unidentified patient samples submitted to ARUP laboratories (Salt Lake City, Utah) for testing. All studies with human samples are approved by the Institutional Review Board of the University of Utah. An assessment of within and between run imprecision is performed by analyzing pools of human serum samples supplemented with Tg. Concentrations of Tg are 2, 6, 14 and 398 ng/mL (3, 9.1, 21.2, 603 pmol/L); the samples are analyzed in three replicates over five days; in addition three quality control samples (QC) samples are analyzed in routine runs over 16 days.

Sensitivity of the method is evaluated by analyzing serum samples containing progressively lower concentration of Tg. Five samples (range 0.26-3.9 ng/mL) are prepared by serial dilution of serum pool containing 3.9 ng/mL (5.9 pmol/L) with a serum pool not containing Tg, the samples are analyzed in duplicate over two days.

Linearity of the method is evaluated by analyzing seven samples prepared by mixing in different proportions two serum pools containing 5 and 1045 ng/mL (3.3 and 886 pmol/L) of Tg. The samples are analyzed in duplicate over two days. Blank samples are injected after high standards to evaluate carryover potential of the method.

Lower limit of quantification (LOQ) and upper limit of linearity (ULOL) are determined as the lowest concentrations at which accuracy is within ±15%, imprecision is <15% and a ratio of the mass transitions is maintained at ±30%. Limit of detection (LOD) is the lowest concentration at which chromatographic peaks are present in all mass transitions and signal to noise ratio was >5.

The method is compared with the Access Beckman Coulter DxI800 Tg immunoassay performed at ARUP Laboratories. Two types of samples are used for the comparison: samples tested negative for Tg-AAb (n=73), and samples tested positive for Tg-AAb (n=113). Samples with concentration of Tg-AAb below 20 IU/mL are considered as Tg-AAb negative. Ratio of the concentrations determined from multiple mass transitions is used for evaluation of the specificity of analysis.

Magnetic beads enrichment recovery is determined by performing affinity enrichment of a pool of digested serum samples containing 80 ng/mL of Tg. IS is added before enrichment to three samples, and to another three samples after the enrichment. The difference between the observed concentrations of Tg in the pre- and post-enrichment spiked samples gives a measure of the recovery.

Sample dilution is evaluated by analyzing serum sample containing over 3000 ng/mL of Tg analyzed with dilution factors (5, 10, 20, 30, and 50).

Effect of lipemia, hemolysis and icterus is evaluated by analyzing pools of 'normal' serum, lipemic, hemolized and ichteric samples 'as is', and mixed in ratio 1:1 ('normal' serum/lipemic; 'normal' serum/hemolized; and 'normal' serum/icteric) and concentrations are compared with concentrations measured in the individual samples.

Ion suppression is evaluated using post column infusion method (Matuzevsky et al., 2003, *Strategies for the assessment of matrix effect in quantitative bioanalytical methods based on HPLC-MS/MS*, Anal Chem 75:3019-3030, incorporated herein by reference). A set of patient samples free of Tg is analyzed by the method, while standard of VIFDAN-APVAVR (SEQ ID 001) peptide (100 ng/mL, flow rate 5 µL/min) is infused into the effluent of the analytical column. The chromatograms are inspected for signs of ion suppression.

Blood from five volunteers is collected in potassium EDTA, sodium heparin, serum and serum separation tubes and the samples are analyzed by the method. Concentrations observed in the samples are compared within each individual.

Storage stability of thyroglobulin is evaluated with purpose of finding acceptable storage conditions. Aliquots of human serum pool are stored at room temperature, in refrigerator (4° C.), and in freezer (−20° C.); the tubes are placed into a −70° C. freezer after 1, 2, 3, 4, 8, 14, 21 and 28 days of storage and analyzed in a single batch.

Reference interval study for Tg is performed with samples from self-reported healthy adult volunteers (25 men and 25 women) and 140 samples from children ages 1-17 (1, 4, 7, 10, 13, and 16 year old, 10 samples from boys and 10 samples from girls of the above ages). The volunteers are without chronic diseases, and not on thyroid medications; the blood is collected in serum separation tubes, serum is separated, and the samples are stored at −70° C.

Example 7

Method Validation

Assay specificity is demonstrated by analyzing over 500 human serum and plasma patient samples and evaluating quality of the chromatographic peaks and ratios of the mass transitions used. Cross-contribution of the mass transitions used for Tg and the internal standard is evaluated by analyzing plasma samples containing internal standard (100 pg/mL) in samples not containing Tg (n=5), and plasma samples containing Tg above 500 ng/mL (0.76 pmol/L) in the absence of internal standard (n=10). No signal cross-contribution is observed on the chromatograms.

An assessment of within and between run imprecision is performed by analyzing human serum samples containing Tg at concentrations 8, 20 and 480 ng/mL. As shown in Table 1, the assay imprecision at the evaluated concentrations is less than 11%. The LOQ and LOD of the method are 0.5 and 0.25 ng/mL, respectively; signal-to-noise ratio of the mass transition m/z 636.36/1059.56 at the LOQ is >10.

Figure 5:
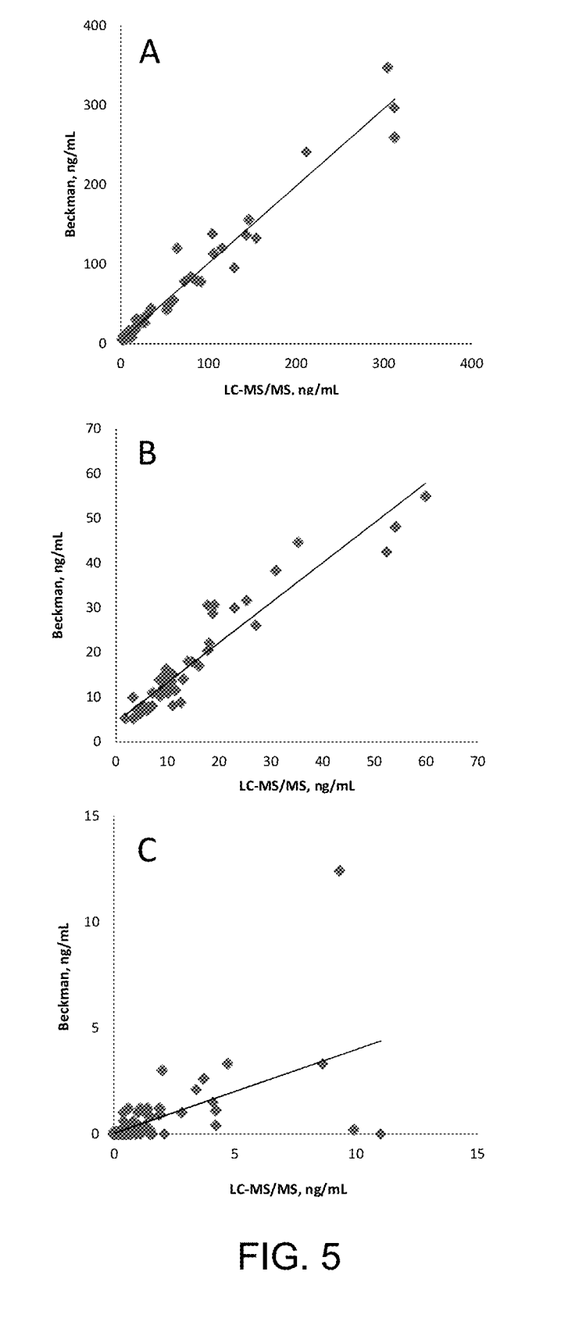
FIG. 5 shows results of LC-MS/MS method comparison with a Beckman Coulter Access analyzer for thyroglobulin autoantibody negative (A, B) and thyroglobulin autoantibody positive samples (C). Thyroglobulin concentrations 0-350 ng/mL (A), thyroglobulin concentrations below 60 ng/mL (B); according to one aspect of the present disclosure.

To evaluate dilution integrity, at concentrations above the upper limit of linearity of the method, subject serum samples containing 2425 ng/mL of Tg are diluted with serum not containing Tg using 5, 10, 20, 30, 50, and 100-fold dilution, and each sample is analyzed in duplicate. Concentrations observed in the samples agree with each other to within 10%. Results of the method comparison with Access analyzer (Beckman Coulter) (FIG. 5) show Deming regression IA=1.01*LC-MS/MS−1.67, r=0.974, Sy/x=9.37. The observed precision and accuracy of the method meet the acceptance criteria for diagnostic tests of small molecules. FIG. 5 shows results of the LC-MS/MS method comparison with Access analyzer (Beckman Coulter) using Tg-AAb negative (A, B) and Tg-AAb positive samples (C). (A) Concentrations 0-350 ng/mL IA=1.00*LC-MS/MS−2.3, r=0.982, Sy,x=9.5; (B) Concentrations <60 ng/mL. IA=1.01*LC-MS/MS−2.1, r=0.956, Sy,x=2.8; (C) IA=0.53*LC-MS/MS−0.1, r=0.586, Sy,x=1.1.

A set of 113 samples tested positive for Tg-AAb (Tg-AAb concentration range 19-1740 IU/mL; Tg recovery test results 27-97%) are analyzed by LC-MS/MS and the concentrations are compared to the concentrations determined using a Beckman Coulter Access analyzer (FIG. 5C). Concentrations of Tg measured by this method are higher than values determined by immunoassay. Difference in concentrations is caused by the presence in the samples of Tg-AAb that interferes with the immunoassay. The results suggest that the mass spectrometry based test overcomes interference of Tg-AAb and would allow detecting recurrence of thyroid cancer in subjects having Tg-AAb earlier during the course of disease than the immunoassays.

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method for determining a concentration of thyroglobulin in a biological sample, comprising performing the following steps in sequential order:
   first, providing a biological sample including unbound thyroglobulin and endogenous autoantibody-bound thyroglobulin;
   second, adding an immunoglobulin antibody specific for thyroglobulin to the biological sample containing the endogenous autoantibody-bound thyroglobulin such that the unbound thyroglobulin binds with the immunoglobulin antibody to form antibody-bound thyroglobulin;
   third, enriching the antibody-bound thyroglobulin and the endogenous autoantibody-bound thyroglobulin present in the biological sample to form an enriched fraction of the thyroglobulin, wherein the enriching step is performed by precipitating the antibody-bound thyroglobulin and autoantibody bound thyroglobulin with ammonium sulfate;
   fourth, identifying the thyroglobulin in the enriched fraction, wherein identifying the thyroglobulin in the enriched fraction further includes digesting the antibody-bound thyroglobulin and the endogenous autoantibody-bound thyroglobulin complexes, and detecting a product of digestion to identify thyroglobulin by mass spectrometry; and
   fifth, determining the concentration of the thyroglobulin in the biological sample.

2. The method of claim 1, wherein the mass spectrometry is tandem mass spectrometry.

3. The method of claim 1, wherein the mass spectrometry is high resolution and high mass accuracy mass spectrometry.

4. The method of claim 1, wherein the product of digestion of thyroglobulin is a peptide selected from the group consisting of SEQ ID 001, SEQ ID 002, SEQ ID 003, SEQ ID 004, SEQ ID 005, and a combination thereof.

* * * * *